(12) United States Patent
Mayer et al.

(10) Patent No.: US 8,153,082 B2
(45) Date of Patent: Apr. 10, 2012

(54) SHEET CONFIGURED WITH A TESSELLATED ZIPPER PATTERN OF IDENTICALLY SHAPED SENSOR ELEMENTS AND METHOD OF MANUFACTURE

(75) Inventors: Daniel W. Mayer, Wyoming, MN (US); Michael Howe, Blaine, MN (US)

(73) Assignee: Mocon, Inc., Minneapolis, MN (US)

( * ) Notice: Subject to any disclaimer, the term of this patent is extended or adjusted under 35 U.S.C. 154(b) by 267 days.

(21) Appl. No.: 12/630,058

(22) Filed: Dec. 3, 2009

(65) Prior Publication Data

US 2011/0135545 A1 Jun. 9, 2011

(51) Int. Cl.
*G01N 21/00* (2006.01)
(52) U.S. Cl. ........ 422/425; 422/420; 422/424; 156/250; 428/195.1
(58) Field of Classification Search .................. None
See application file for completion search history.

(56) References Cited

U.S. PATENT DOCUMENTS

| 6,935,997 | B2 | 8/2005 | Kling |
| 2003/0024811 | A1 | 2/2003 | Davies et al. |
| 2008/0090429 | A1 | 4/2008 | Mok et al. |

OTHER PUBLICATIONS

Fitzgerald, M. et al., Nondestructive Monitoring of Oxygen Profiles in Packaged Foods Using Phase-Fluorimetric Oxygen Sensor, Institute of Food Technologists, Journal of Food Science (JFS) Food Engineering and Physical Properties, vol. 66, No. 1, 2001.

*Primary Examiner* — In Suk Bullock
*Assistant Examiner* — Timothy G Kingan
(74) *Attorney, Agent, or Firm* — Sherrill Law Offices, PLLC

(57) ABSTRACT

A sheet of sensors and a method of manufacturing such sheet of sensors. The sheet is configured with (A) a tessellated zipper pattern of identically shaped elements defining (i) a right longitudinal column consisting of a base portion of a right set of elements, (ii) a left longitudinal column consisting of a base portion of a left set of elements, and (iii) an intermediate longitudinal column consisting of alternating tab portions of the right and left elements, and (B) a continuous longitudinal strip of functional material positioned only within the intermediate column.

16 Claims, 4 Drawing Sheets

SHEET CONFIGURED WITH A TESSELLATED ZIPPER PATTERN OF IDENTICALLY SHAPED SENSOR ELEMENTS AND METHOD OF MANUFACTURE

BACKGROUND

It is often necessary to place a spot of a functional material onto a surface for use as a sensor to detect and measure a condition (e.g., temperature, pressure, RH, pH, concentration of a target analyte such as O2, O3, CO2, CO, etc) within a confined space (e.g., a carbonated beverage bottle, a food container, a Petri dish, a sealed shipping container, etc.). Due to the expense of most functional materials, it is generally desirable to employ as little functional material as necessary, often resulting in a spot that is less than 100 mm$^2$, typically less than 25 mm$^2$ and often less than 10 mm$^2$.

Handling of such small elements is difficult, especially when direct contact with the functional material is to be avoided in an effort to avoid contaminating or damaging the functional material.

Accordingly, a substantial need exists for an inexpensive source of functional material sensors that is easily manufactured, easily handled and easily applied.

SUMMARY OF THE INVENTION

A first aspect of the invention is an article of commerce. The article of commerce is a sheet configured with (A) a tessellated zipper pattern of identically shaped elements defining (i) a right longitudinal column consisting of a base portion of a right set of elements, (ii) a left longitudinal column consisting of a base portion of a left set of elements, and (iii) an intermediate longitudinal column consisting of alternating tab portions of the right and left elements, and (B) a continuous longitudinal strip of functional material coated onto the sheet within the intermediate column only, whereby a layer of functional material is provided only on the tab portions of the right and left elements.

A second aspect of the invention is a method of manufacturing an article of commerce. The method includes the steps of (1) placing a continuous longitudinal strip of functional material onto a web, and (2) cutting the web into a tessellated zipper pattern of elements, so as to define a pattern including (i) a right longitudinal column consisting of a base portion of a right set of elements, (ii) a left longitudinal column consisting of a base portion of a left set of elements, and (iii) an intermediate longitudinal column consisting of alternating tab portions of the right and left elements, wherein the longitudinal strip of functional material is retained within the intermediate column only so as to be present only on the tab portions of the right and left elements.

DETAILED DESCRIPTION OF A PREFERRED EMBODIMENT

Nomenclature

| | |
|---|---|
| 10 | Card |
| 20 | Array of Elements |
| 21r | Right Column |
| 21s | Left Column |
| 21i | Intermediate Column |
| 30 | Elements |
| 30r | Right Elements |
| 30s | Left Elements |
| 31 | Base Portion of Elements |
| 32 | Tab Portion of Elements |
| 40 | Backing Layer |
| 50 | Pressure Sensitive Adhesive |
| 60 | Support Layer |
| 70 | Layer of Functional Material |
| 70r | Right Edge of Layer of Functional Material |
| 70s | Left Edge of Layer of Functional Material |
| 71r | Margin Between Right Edge of Layer of Functional Material and Right Column |
| 71s | Margin Between Left Edge of Layer of Functional Material and Left Column |
| 80 | Release Liner |

Definitions

As utilized herein, including the claims, the term "sheet" means something that is thin in comparison to its length and breadth, typically with an aspect ratio of more than 100 to 1.

As utilized herein, including the claims, the term "tessellated" means a pattern of shapes or figures that fill a plane with no overlaps and no gaps.

As utilized herein, including the claims, the term "web" means a continuous sheet, encompassing both a continuous roll and a series of shingled individual sheets.

As utilized herein, including the claims, the phrase "zipper pattern" means a pair of columns with intermeshing elements.

Description

Construction

Figure 1:
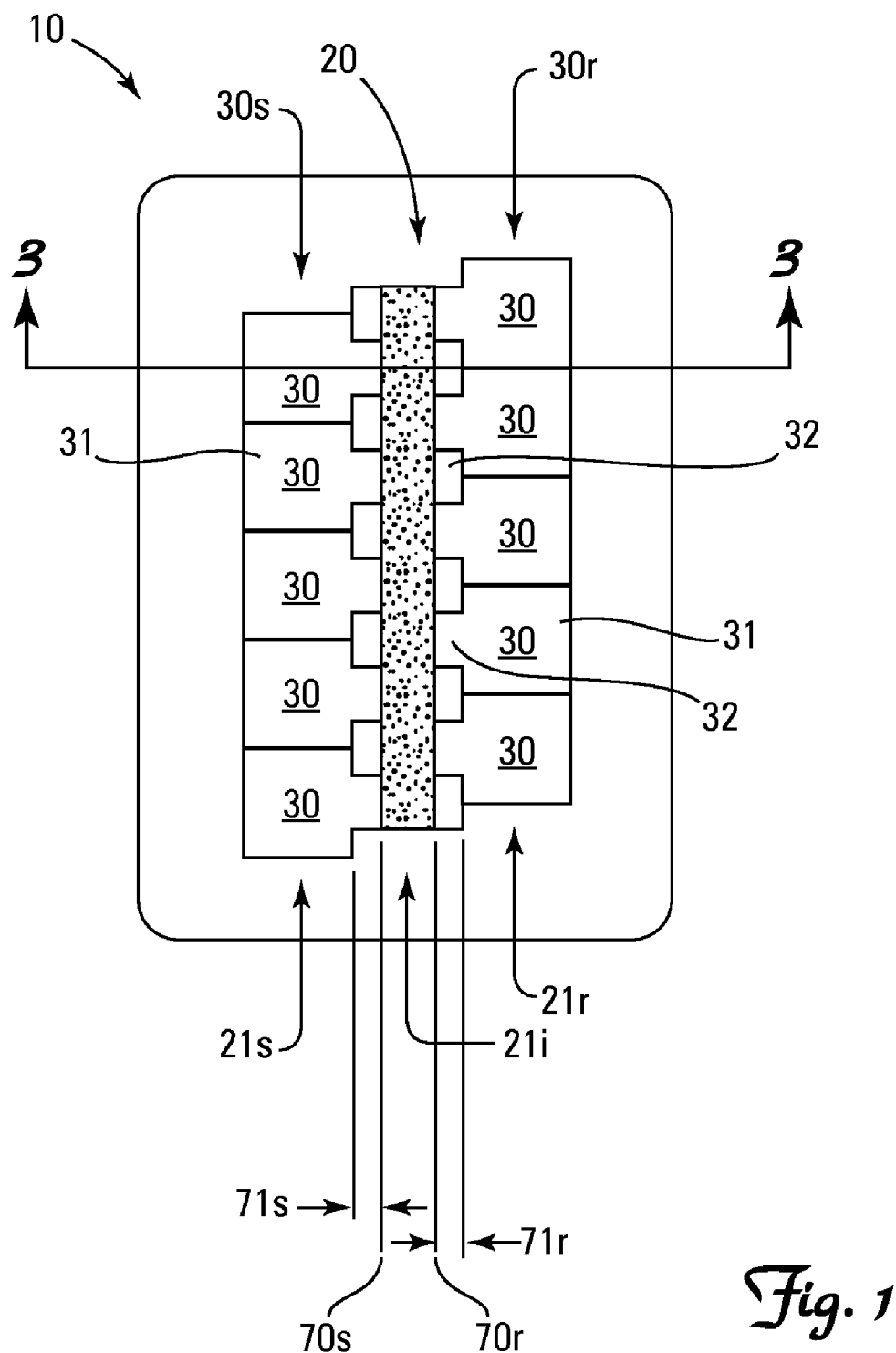
FIG. 1 is a top view of one embodiment of the invention with a complete coating of functional material.
Figure 2:
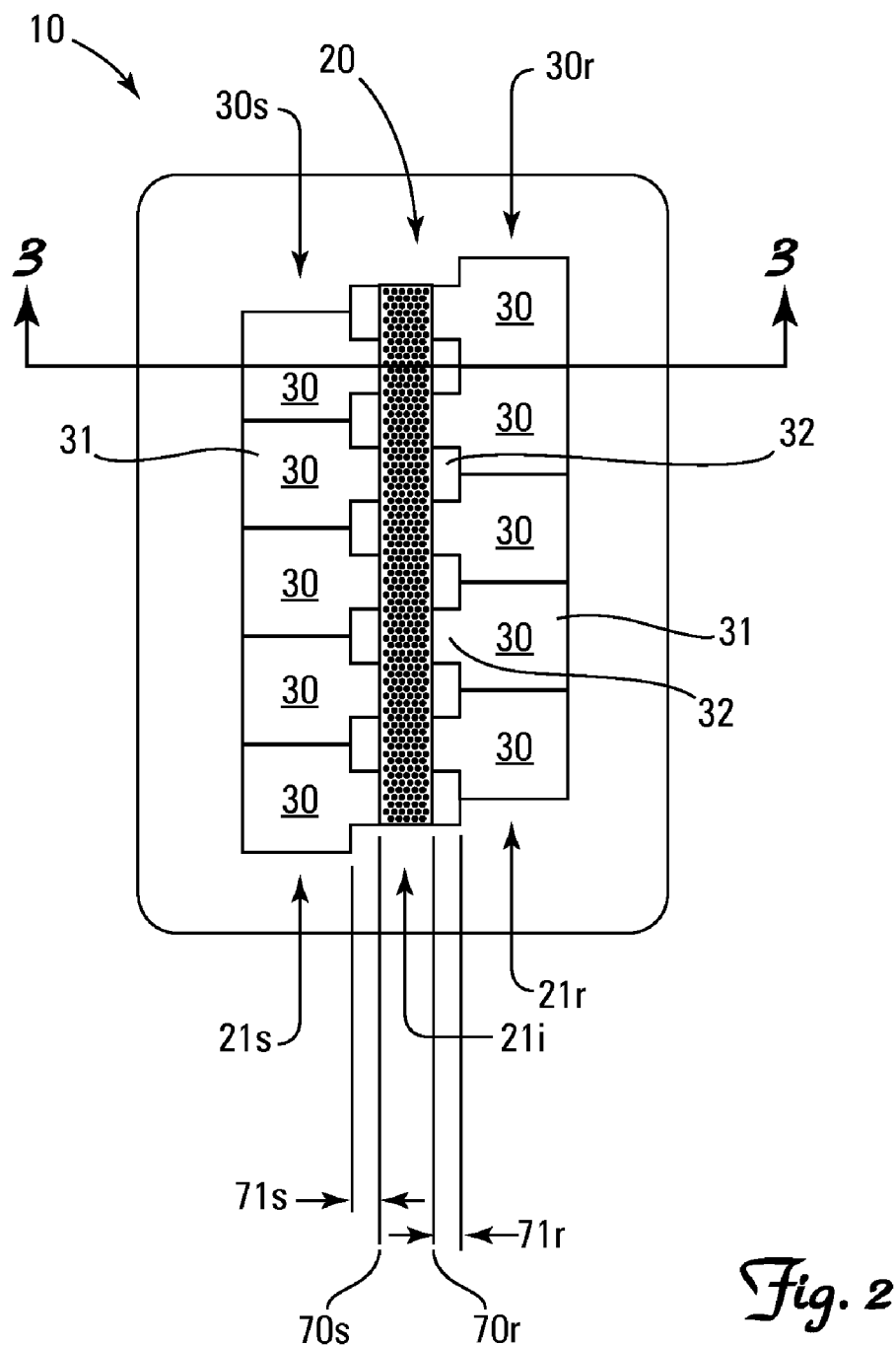
FIG. 2 is a top view of another embodiment of the invention with a pattern coating of functional material.

Referring generally to FIGS. 1 and 2, the invention is a sheet, preferably a card 10 that is about 2 to 4 inches by about 2 to 6 inches, into which has been formed a tessellated zipper pattern or array 20 of identically shaped elements 30. The array defines (i) a right longitudinal column 21r consisting of a base portion 31 of a right set of elements 30r, (ii) a left longitudinal column 21s consisting of a base portion 31 of a left set of elements 30s, and (iii) an intermediate longitudinal column 21i consisting of alternating tab portions 32 of the right 30r and left 30s elements.

Figure 4A:
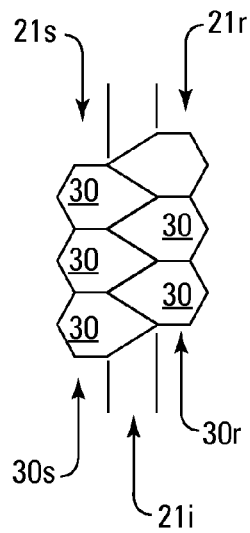
FIGS. 4A-C depicted alternative tessellation patterns suitable for use in the present invention.
Figure 4B:
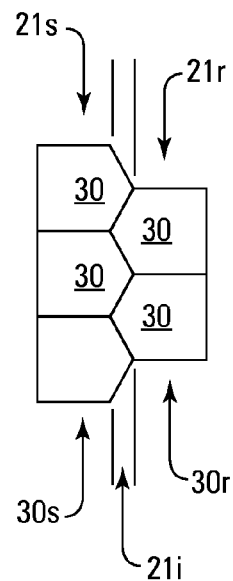
Figure 4C:
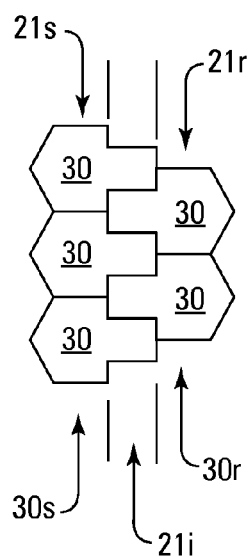

The elements 30 may be given any desired shape capable of formed a tessellated zipper pattern or array 20 of identically shaped elements 30. A T-shaped element 30 is shown in FIGS. 1 and 2. Many other shapes can be employed, with a few depicted in FIGS. 4A (teardrop), 4B (sales tag) and 4C (arrowhead).

Figure 3:
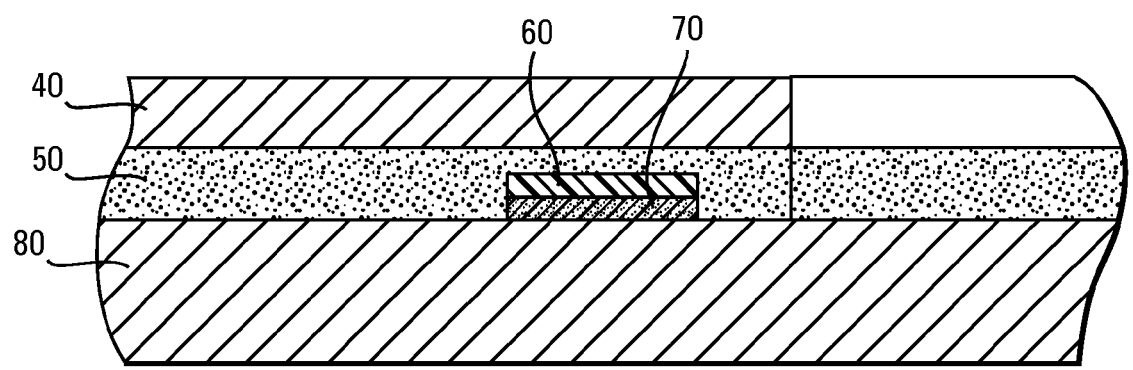
FIG. 3 is an enlarged cross-sectional side view of the invention shown in FIG. 1 taken along line 3-3.

Referring to FIG. 3, the card 10 includes a backing layer 40 with a layer of a pressure sensitive adhesive 50 coated over an inner major surface (unnumbered) of the backing layer 40.

The backing layer 40 may be manufactured from substantially any material capable of providing the necessary structural integrity, including specifically but not exclusively, paper, cardstock, cardboard, polymeric sheets, metal sheets, etc. The preferred backing layer based predominantly upon price is cardstock.

The adhesive 50 may be selected from any of the widely available pressure sensitive adhesives capable of providing the desired level of adhesion to the target surface for the desired duration. One of ordinary routine skill in the art would be able to select a suitable adhesive once apprised of the nature and typical orientation of the surface to which the element 30 is to be adhered (e.g., a vertically disposed smooth inner surface of a PET bottle for at least 48 hours or a horizontally disposed rough surface of an abrasive drywall sanding pad for at least 2 hours).

A continuous longitudinal strip of functional material 70 is coated along the longitudinal length of the intermediate column 21i. This provides a layer of functional material 70 on each element 30 that is limited to the tab portion 32 of both the right 30r and left 30s elements. This permits a user to grasp the base portion 31 of each element 30 for purposes of removing the element 30 from the card 10 and applying the element 30 to a target surface (not shown), without directly contacting and thereby risking contamination of the functional material 70. The strip of functional material 70 is preferably laterally offset from the right 21r and left 21s columns, so as to provide right 71r and left 71s margins between the right 70r and left 70s edges of the strip of functional material 70 and the base portion 31 of the elements 30 that is devoid of functional material 70. This provides additional protection against undesired coating of the base portions 31 of the elements 30 with functional material 70.

For certain applications it may be necessary or desired to first coat the functional material 70 onto a support layer 60 and then laminating the support layer 60 onto the adhesive layer 50 with the layer of functional material 70 on the exposed major surface (unnumbered) of the support layer 60 facing away from the adhesive layer 50.

A release liner 80 is preferably provided for releasably protecting the exposed surface of the adhesive layer 50 and the layer of functional material 70 from wear, tear and contamination until each element 30 is peeled from the card 10 for application to a target surface. Suitable release liners 80 are widely available from a number of sources. One of ordinary routine skill in the art would be able to select a suitable release liner 80 based upon the type of adhesive 50 employed.

The functional material 70 may be any composition or compound that exhibits a detectable and preferably measurable physical, electrical or chemical change under certain defined circumstances (e.g., changes color upon exposure to an acidic environment, emits an electrical signal upon exposure to a target analyte, luminescence is quenched upon exposure to a target analyte, temperature increases due to an exothermic reaction that occurs upon exposure to a target analyte, etc.). The invention is particularly well suited for forming elements 30 functional as photo luminescent sensors by employing an analyte quenched luminescent compound, such as a ruthenium-based luminescence indicator or a platinum or palladium porphyrin luminescence indicator, as the functional material 70. Such luminescence compositions are well known and widely available from a number of commercial sources. Disclosure of various suitable analyte quenched ruthenium-based luminescence compositions is provided in International Patent Application Publication No. 2007/120637 to Oxy-Sence, Inc. Disclosure of various suitable analyte quenched platinum and palladium porphyrin luminescence compositions in provided in United States Patent Application Publication No. 20060002822 to Luxcel Biosciences Ltd.

Manufacture

The card 10 can be manufactured by employing traditional web line converting processes and techniques to laminate the backing layer 40, adhesive layer 50, layer of functional material 70 and release liner 80. The tessellated zipper pattern of elements 30 can be cut into the card 10 at any time during the converting process, but is most suitably performed after the layers have been fully integrated and at the same time that the individual cards 10 are cut from the web.

Use

Individual elements 30 (typically called sensors) can be used by simply bending the card to delaminate a corner (unnumbered) of one of the elements 30 from the release liner 80, pinching the exposed corner between the pointer finger and the thumb, peeling the element 30 from the card 10, and adhering the element 30 to a target surface such as the inside of a transparent or translucent area on a food container (not shown) with the functional material 70 visible through the container (not shown) so that the functional material 70 can be read by an appropriate instrument (not shown).

We claim:

1. An article of commerce, comprising:
   (a) a sheet configured with a tessellated zipper pattern of identically shaped elements defining (i) a right longitudinal column consisting of a base portion of a right set of elements, (ii) a left longitudinal column consisting of a base portion of a left set of elements, and (iii) an intermediate longitudinal column consisting of alternating tab portions of the right and left elements,
   (b) a continuous longitudinal strip of functional material coated onto the sheet within the intermediate column only, whereby a layer of functional material is provided only on the tab portions of the right and left elements.

2. The article of claim 1 wherein the sheet is comprised of at least a backing layer, and the article further comprises a layer of a pressure sensitive adhesive so as to form sequential layers of backing, pressure sensitive adhesive and functional material.

3. The article of claim 1 wherein the right and left elements are mirror images of one another.

4. The article of claim 1 wherein the strip of functional material is laterally offset from the right and left columns, whereby a margin devoid of functional material is provided on the tab portion of each element proximate the base portion.

5. The article of claim 1 wherein the functional material is an analyte-quenchable photo luminescent substance suitable for use as an analyte sensor.

6. The article of claim 5 wherein the analyte-quenchable photo luminescent substance is platinum porphyrin.

7. The article of claim 1 wherein the layer of functional material is a pattern coated layer.

8. The article of claim 1 wherein the layer of functional material is a complete coverage layer.

9. A method of manufacturing an article of commerce, comprising:
   (a) placing a continuous longitudinal strip of functional material onto a web, and
   (b) cutting the web into a tessellated zipper pattern of elements, so as to define a pattern including (i) a right longitudinal column consisting of a base portion of a right set of elements, (ii) a left longitudinal column consisting of a base portion of a left set of elements, and (iii) an intermediate longitudinal column consisting of alternating tab portions of the right and left elements, wherein the longitudinal strip of functional material is retained within the intermediate column only so as to be present only on the tab portions of the right and left elements.

10. The method of claim 9 further comprising the step of coating the web with a layer of a pressure sensitive adhesive, with the layer of functional material adhered to the web by the layer of adhesive.

11. The method of claim 9 wherein the right and left elements are mirror images of one another.

12. The method of claim 9 wherein the strip of functional material is laterally offset from the right and left columns, whereby a margin devoid of functional material is provided on the tab portion of each element proximate the base portion.

13. The method of claim 9 wherein the functional material is an analyte-quenchable photo luminescent substance suitable for use as an analyte sensor.

14. The method of claim 13 wherein the analyte-quenchable photo luminescent substance is platinum porphyrin.

15. The method of claim 9 wherein the functional material is a pattern coated layer.

16. The method of claim 9 wherein the layer of functional material is an complete coverage layer.

\* \* \* \* \*